US007904250B2

(12) United States Patent
Molla et al.

(10) Patent No.: US 7,904,250 B2
(45) Date of Patent: Mar. 8, 2011

(54) COMPUTER SOFTWARE TO ASSIST IN IDENTIFYING SNPS WITH MICROARRAYS

(75) Inventors: Michael Molla, Madison, WI (US); Todd Richmond, Madison, WI (US); Steven Smith, Fitchburg, WI (US); Thomas Albert, Fitchburg, WI (US)

(73) Assignee: Roche Nimblegen, Inc., Wilmington, DE (US)

( * ) Notice: Subject to any disclaimer, the term of this patent is extended or adjusted under 35 U.S.C. 154(b) by 838 days.

(21) Appl. No.: 11/043,294

(22) Filed: Jan. 26, 2005

(65) Prior Publication Data

US 2006/0014164 A1 Jan. 19, 2006

Related U.S. Application Data

(60) Provisional application No. 60/539,220, filed on Jan. 26, 2004.

(51) Int. Cl.
*G01N 33/50* (2006.01)
(52) U.S. Cl. .......................................... 702/20; 977/792
(58) Field of Classification Search .................. None
See application file for complete search history.

(56) References Cited

U.S. PATENT DOCUMENTS

| 5,143,854 A | 9/1992 | Pirrung et al. |
| 6,375,903 B1 | 4/2002 | Cerrina et al. |

OTHER PUBLICATIONS

Domeniconi et al. (Proceedings of the Eighteenth International Conference on Machine Learning, p. 98-105, 2001).*
Wang et al. (Science, vol. 280, p. 1078-1082, May 15, 1998).*
Hacia et al., "Detection of heterozygous mutations in BCRA1 using high density oligo nucleotide arrays and two-color fluorescence", Nature, vol. 14, p. 441-447, 1996.*
Kozal et al., "Extensive polymorphisms observed in HIV-1 Clade-B protease gene using high-density oligonucleotide arrays", Nature Medicine, vol. 2, No. 7, 753-759, Jul. 1996.*
Chee et al., "Accessing Genetic Information with High-Density DNA Arrays", Science, vol. 274, No. 5287, p. 610-614, Oct. 25, 1996.*
Cutler, D.J., et al., "High-Throughput Variation Detection and Genotyping Using Microarrays," Genome Research 11:1913-1925 (2001).
Hirschhorn, J.N., et al., "SBE-TAGS: An array-based method for efficient single-nucleotide polymorphism genotyping," PNAS 97:12164-12169 (2000).
Molla, M., et al., "A Self-Tuning Method for One-Chip SNP . . . ," The Proceedings of the IEEE Conference on Computational Systems Bioinformatics (CSB 2004).
Nuwaysir, E.F., et al., "Gene Expression Analysis Using Oligonucleotide Arrays Produced by Maskless Photolithography," Genome Research 12:1749-1755 (2002).
Ruan, Y., et al., "Comparative full-length genome sequence analysis of 14 SARS coronavirus isolates and common mutations . . . ," The Lancet 361:1779-1785 (2003).
Singh-Gasson, S., et al., "Maskless fabrication of light-directed oligonucleotide microarrays using a digital micromirror array," Nature Biology 17:974-978 (1999).
Wang, D.G., et al., "Large-scale identification, mapping, and genotyping of single-nucleotide polymorphisms in the human genome," Science 280:1077-1082 (1998).

* cited by examiner

*Primary Examiner* — Karlheinz R Skowronek
(74) *Attorney, Agent, or Firm* — Quarles & Brady LLP (57) ABSTRACT

The present invention is a method to assist in the identification of single nucleotide polymorphisms (SNP) from microarray hybridization data. Data from hybridization protocols run on microarrays often have variations in the data resulting from variations in hybridization conditions and efficiencies and variations in optical intensities. An algorithm is described to screen the results to identify those data points most likely to be real SNPs as opposed to variations in the hybridization or sensing data.

4 Claims, 5 Drawing Sheets

Figure 1. Casting SNP Identification as a Classification Task

Figure 2. Learning by Proxy Category

Figure 3. Choosing K

Figure 4: ROC Curve for SARS SNP Detection

Figure 5: Call Rate vs. SNP Detection Rate

SEQUENCE LISTING

<160> NUMBER OF SEQ ID NOS: 5

<210> SEQ ID NO 1
<211> LENGTH: 26
<212> TYPE: DNA
<213> ORGANISM: Artificial
<220> FEATURE:
<223> OTHER INFORMATION: Synthetic oligonucleotide

```
<400> SEQUENCE: 1
ctgacatgca gctatgcatg catgaa                                              26

<210> SEQ ID NO 2
<211> LENGTH: 26
<212> TYPE: DNA
<213> ORGANISM: Artificial
<220> FEATURE:
<223> OTHER INFORMATION: Synthetic oligonucleotide

<400> SEQUENCE: 2
gactgtacgt cgatacgtac gtactt                                              26

<210> SEQ ID NO 3
<211> LENGTH: 26
<212> TYPE: DNA
<213> ORGANISM: Artificial
<220> FEATURE:
<223> OTHER INFORMATION: Synthetic oligonucleotide

<400> SEQUENCE: 3
gactgtacgt cgaaacgtac gtactt                                              26

<210> SEQ ID NO 4
<211> LENGTH: 26
<212> TYPE: DNA
<213> ORGANISM: Artificial
<220> FEATURE:
<223> OTHER INFORMATION: Synthetic oligonucleotide

<400> SEQUENCE: 4
gactgtacgt cgacacgtac gtactt                                              26

<210> SEQ ID NO 5
<211> LENGTH: 26
<212> TYPE: DNA
<213> ORGANISM: Artificial
<220> FEATURE:
<223> OTHER INFORMATION: Synthetic oligonucleotide

<400> SEQUENCE: 5
gactgtacgt cgagacgtac gtactt                                              26
```

COMPUTER SOFTWARE TO ASSIST IN IDENTIFYING SNPS WITH MICROARRAYS

CROSS-REFERENCE TO RELATED APPLICATIONS

This application claims priority from U.S. provisional patent application No. 60/539,220 filed Jan. 26, 2004.

STATEMENT REGARDING FEDERALLY SPONSORED RESEARCH OR DEVELOPMENT

Not applicable.

BACKGROUND OF THE INVENTION

The advent of DNA microarray technology makes it possible to build an array of hundreds of thousands of DNA sequences in a very small area, such as the size of a microscopic slide. See, e.g., U.S. Pat. No. 6,375,903 and U.S. Pat. No. 5,143,854, each of which is hereby incorporated by reference in its entirety. The disclosure of U.S. Pat. No. 6,375,903 enables the construction of so-called maskless array synthesizer (MAS) instruments in which light is used to direct synthesis of the DNA sequences, the light direction being performed using a digital micromirror device (DMD), also known as a digital light processor (DLP). Using an MAS instrument, the selection of DNA sequences to be constructed in the microarray is under software control so that individually customized arrays can be built to order. In general, MAS based DNA microarray synthesis technology allows for the parallel synthesis of over 800,000 unique oligonucleotides in a very small area of on a standard microscope slide. The microarrays are generally synthesized by using light to direct which oligonucleotides are synthesized at specific locations on an array, these locations being called features. Typically, one nucleotide sequence is synthesized at each feature of the array, i.e. there are multiple probes in each feature, but all those probes have the same nucleotide sequence. For certain applications it would be advantageous to have oligonucleotides of different sequences present within one feature of the array, and be able to control the ratio and direction (5'-3', or 3'-5') of these oligonucleotides.

One use of microarrays is to perform sequence analysis of DNA isolated from living organisms. Science has now made available generalized DNA sequences of the entire genomes of several important organisms, including humans. One technique that can be used to identify a genetic variant is to sequence the genomic DNA of an individual and then to compare that sequence to the reference sequence of that organism. It has been found that many differences in DNA sequence are presented as single variations in DNA sequence, often referred to as single nucleotide polymorphisms or SNPs. By performing a sequence comparison between the entire sequenced genome of an individual and the reference genome of that species, it is by this brute force mechanism to identify the SNPs for that individual. However, this process is too laborious to be practical for SNP detection on a large scale. The identification and analysis of SNPs is therefore a technology to which much attention has been devoted.

BRIEF SUMMARY OF THE INVENTION

The present invention is summarized as a method for identifying single nucleotide polymorphisms from microarray hybridization data, the data being used as a resequencing procedure. The method includes the steps of organizing the data into groups each of which represents all the observed variations in sequence at a single nucleotide location; classifying each group as a conformer or nonconformer depending on whether the highest intensity probes for the single nucleotide position conforms or does not conform to the reference sequence at that location; mapping the conformers and nonconformers in a feature space; and identifying as possible SNPs only those nonconformers which are located in parts of the feature space of the microarray data densely populated with conformers.

The method is based on machine learning and is neutral as to the biochemistry of the particular hybridizations, and hence will improve in its predictability over time. The method is capable of discerning real SNPs from noise in a single experiment.

Other objects advantages and features of the present invention will become apparent from the following specification.

DETAILED DESCRIPTION OF THE INVENTION

The method of efficient genomic resequencing described here has shown significant results and utilizes oligonucleotide microarray technology for its input information. In particular, this type of resequencing begins with a microarray, or chip, which consists of a complete tiling of the reference sequence. Microarrays have oligonucleotide probes arranges in areas referred to as features. The terminology of complete tiling with regard to a chip or microarray means is that the chip has at least one feature which contains probes corresponding exactly to each 25-mer in the reference sequence. In addition, the tiling chip also contains, for each base in this 25-mer reference sequence, three features each of which contains mismatch probes with a single substituted nucleotide, i.e. a single mismatch. Each mismatch probe corresponds to each possible nucleotide variation or SNP at this position which might or might not be present in a variation of the reference sequence. This tiling resequencing chip is then used in a hybridization procedure against genomic DNA from individuals of the species, and the outcome of the hybridization measured by measuring the optical intensity of fluorescence from labeled DNA from the sample matched to the probe sets in the array. In theory, any time a SNP is present a particular individual genomic sample, the feature with a mismatch probe representing this SNP variant should have a higher measured intensity signal than the corresponding feature for the probe that matches the reference sequence. However, due to unpredictability in signal strength, varying hybridization efficiency and various other sources of noise and error, this method typically results in many base positions whose identities are incorrectly predicted. Current approaches to this problem require extensive parameter tuning involving the analysis of very large amounts of data. This tuning needs to be re-run any time experimental conditions are changed. Another limitation of current methods is that, in order to have a single probe represented by a sufficient number of pixels, a very expensive high-resolution scanner must be used.

Presented here is a technique that uses machine learning to differentiate potential SNPs from chip noise and variations in hybridization conditions. Unlike other methods, our method does not require such a high-resolution scanner and furthermore does not require any tuning outside of the single chip being analyzed. For haploid organisms it produces results similar to the published results in SNP identification rate for the best known of the current statistical methods. Our method uses only the mean signal intensity of each feature on the chip and it requires no data from outside of the chip.

To illustrate this technique, imagine that the immediate task is to identify SNPs in the context of a particular oligonucleotide-microarray-based DNA resequencing process. This type of resequencing consists of fully tiling (making features having probes corresponding to every 25-mer in) the reference sequence of an organism's DNA through a region of interest. For each of these features having probes corresponding to the reference sequence, another three features having single mismatch probes are also created in the microarray. Each of the mismatch probes inserts a different nucleotide base in its center position. For example, if the organism's reference DNA includes the sequence:

```
                                      (SEQ ID NO: 1)
        CTGACATGCAGCTATGCATGCATGAA.
```

Then the feature corresponding reference probe will have this complementary sequence:

```
                                      (SEQ ID NO: 2)
        GACTGTACGTCGATACGTACGTACTT.
```

To perform conventional microarray resequencing, the microarray would then include features with probes having each of the following sequences:

```
                                      (SEQ ID NO: 3)
        GACTGTACGTCGAAACGTACGTACTT.

(SEQ ID NO: 4)
        GACTGTACGTCGACACGTACGTACTT.

(SEQ ID NO: 5)
        GACTGTACGTCGAGACGTACGTACTT.
```

For purposes of this discussion, we call a group of probes such as this that represent all possible SNPs at a given position a position-group or p-group.

The detail of the method of interpreting such a resequencing chip can be summarized as follows: Given the data from a single resequencing chip, representing either the complete genome of an organism, or some region or regions of interest in such a genome, identify, from among the positions at which the sample sequence seems to differ from the reference sequence, which of these positions are likely to be real SNPs rather than noise and return an output which identifies these positions along with a confidence measure for each.

To understand the new approach described here, consider that after the chip has been exposed to the sample, the probes will each have a resulting intensity. (In referring to probes in this description, we mean the set of probes in a feature, and terms probes and features are sometimes used interchangeably below.) Each p-group's set of 4 such intensities is called an example. For most of these examples, the highest of the 4 intensities will be the reference probe, i.e. the probe with no mismatch base. Set forth in Table 1 below is a sample of data from a resequencing process. The resequencing probes are shown at the top of Table 1, followed by the experimentally derived intensity data and the grouping of the data into an example. As shown in Table 1, we illustrate examples for which the highest intensity is found for the reference sequence conformers, as expected. For the purposes of the machine-learning algorithm, we also call the conformers our positive examples. When one of the mismatch probes has the highest intensity of the probes for that nucleotide, the p-group is called a non-conformer. For the purposes of the machine-learning algorithms, we also call the non-conformers our negative examples. Some of these negative examples reflect actual SNPs in the genomic DNA of the individual organism. However, many or most of them are the results of hybridization failures or other types of noise that do not represent an actual SNP in the sample. Determining the difference between actual SNPs and the noise is the objective.

Figure 1:
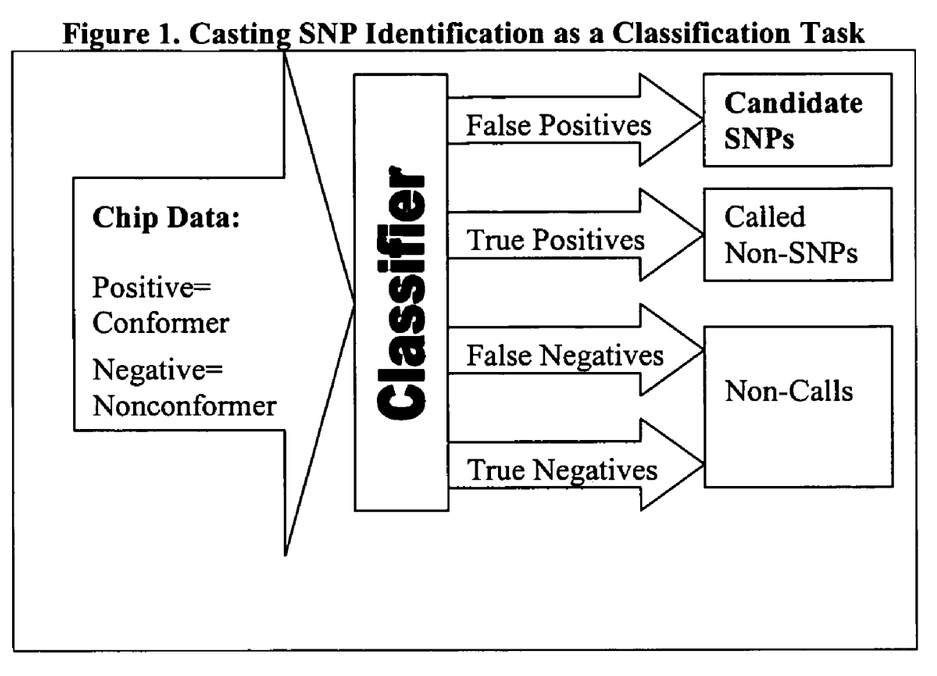
FIG. 1 is a flow chart illustrating the logical flow of information in the present method.

The methodology used to determine this difference is a two-stage process, summarized in Table 2. A key point is that this is a two-stage learning process. First, we do a standard machine-learning experiment to produce and test models of conforming p-groups versus nonconforming p-groups using the available features (features again is the term for an area of the microarray dedicated to a single probe). We then use this as a proxy model for p-groups whose highest intensity base accurately represents the sequence of the sample. As illustrated in FIG. 1, those p-groups that are identified as accurate but indicate something other than the reference base at a given position are called candidate SNPs. We can use this model as such a proxy because we have developed the following two generalized rules, which have held for all of the data that we have seen thus far: 1) The vast majority of negative examples are due to noise in the data. 2) Examples resulting from proper hybridizations will be much nearer to each other in the feature space (described below) than to examples resulting from hybridization failures.

Figure 2:
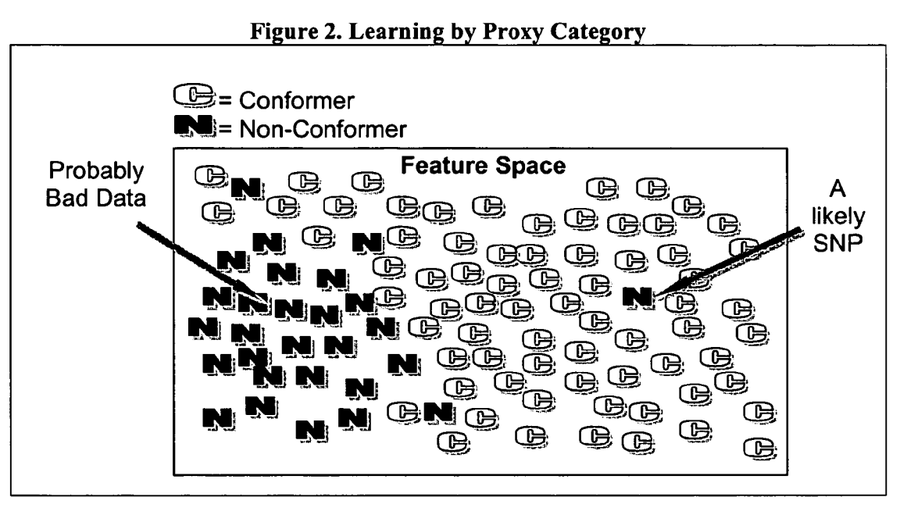
FIG. 2 is an illustration of the concept of the feature space and how the analysis is made of data in the feature space.

Following these rules, an area of feature space dense with positive examples is unlikely to contain probes that are hybridization failures. In fact, the likelihood that any given example in an area is a hybridization error can be roughly estimated by the density of negative examples in that area of feature space. This is illustrated in FIG. 2, where the conformers and non-conformers are placed in their real geometry in the feature space on the microarray, and the identification of a likely real SNP is illustrated by the fact that it is surrounded in physical space by conformers. In other words, the non-conformer in the neighborhood of other non-conformers are not believed, but a non-conformer in a neighborhood of conformers is believed. By performing this estimation for each of the negative examples in the test set, we find an approximate likelihood that the non-conformer is the result of a hybridization error rather than a real SNP in the genome of the individual. Those negative examples with very low likelihood of being hybridization errors, and conversely high likelihood of being a correct reflection of the underlying sequence, are predicted, by this method, to be SNPs. So the model will be dominated by those characteristics that identify a reliable p-group. Theoretically, in cases where the first assumption is not true, the training set could simply be supplemented with data from other chips containing few or no SNPs.

Our approach employs supervised learning, which is learning, from a set of labeled examples, to categorize future examples that are not labeled. Another important feature of our software is that, though this type of learning often requires human-labeled examples, our software does not require the user to label any examples. The categories are determined automatically from the data.

In order to discover which of these negative examples are likely to be actual SNPs, we applied a number of machine-learning algorithms, including Artificial Neural Networks, Decision Trees, and K-Nearest Neighbors, to the problem. In experiments not described here, we found that the best performer was the K-Nearest Neighbors algorithm. K-Nearest-Neighbors is a well-known classification algorithm within the Machine Learning community. It is called a classification algorithm because it is used to classify examples based on known features. This particular algorithm consists of plotting each example in feature space and then, for each of these examples, finding the K other examples nearest to it in this feature space. The categories of these K neighbors dictate the prediction. If greater than some threshold P of these neighbors is a positive example, the prediction is positive. Otherwise, the prediction is negative. The number of positive examples among the K neighbors can further be used as a measure of confidence in the prediction.

The appropriate value for k and useful definitions of nearness and feature space tend to vary between learning tasks. In this case, our feature space is the 5-dimensional space of examples, where 4 of the dimensions correspond to the intensities of the 4 probes in the example and the 5th dimension is the identity of the base at the center position of the probe with the highest intensity in the example. Nearness between two probes is defined as infinite in cases where the two examples differ in the 5th dimension. In all other cases, it is defined as:

$$\text{nearness} = \sum_{4}^{i=1} |p\text{-group1}_i - p\text{-group2}_i|$$

Where p-group$_1$=example 1 and p-group$_2$=example 2 and p-group$_{Ni}$=the intensity of the $i^{th}$ most intense probe in example p-group$_N$.

Figure 3:
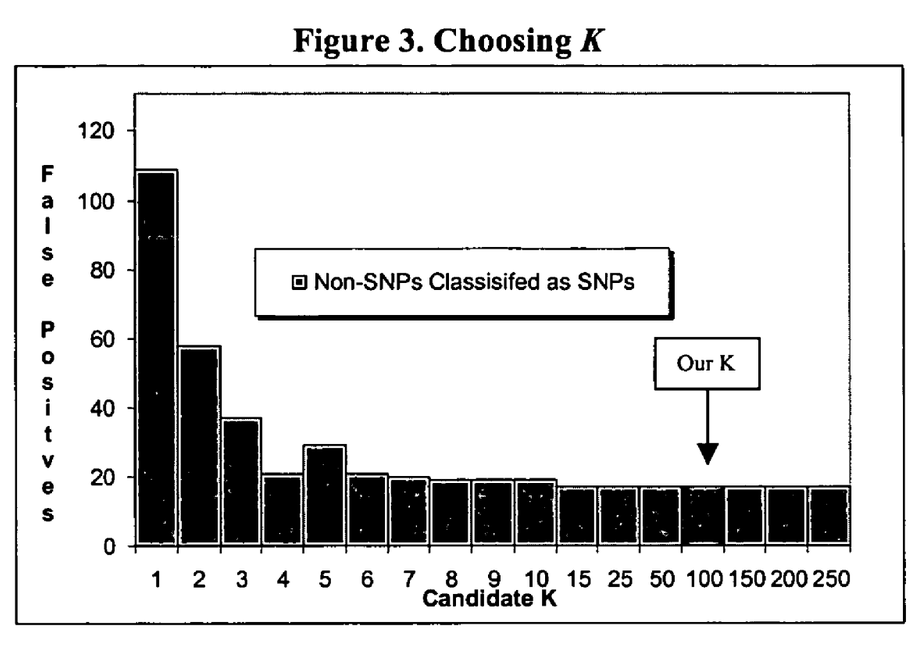
FIG. 3 is a graphical representation of the significance of the choice of a parameter in the algorithm used for machine learning.

In order to choose a good K, we tried various values between one and 250 to see how many false positives would need to have been recorded to identify all of the real SNPs. The results of this test are shown in FIG. 3. Though, as illustrated in FIG. 3, there appears to be a wide range of appropriate values for k, we have chosen k=100.

We use a baseline algorithm to compare the highest intensity probe to the second highest intensity probe. This algorithm is described in Table 3. If the ratio is above a threshold value, we assume that the base represented by the highest intensity probe is the base in the sequence. If this p-group is a non-conformer, our baseline algorithm call it a candidate SNP.

Example

In order to evaluate the algorithm, we chose a useful realistic task. One strain of the SARS virus has been completely sequenced via standard capillary sequencing. We were supplied with a different sample strain. This sample differed in genetic sequence from the reference to an unknown degree. Our task was to identify candidate SNPs from among these variations. Our predictions would subsequently be evaluated using further capillary sequencing and various other laboratory methods.

Using the reference sequence, we designed a resequencing chip including both the forward and reverse strands of this virus. We then exposed this chip to nucleic acids from the sample of the new virus. Then we used our algorithm to predict the SNPs on this chip. Once these results were obtained, we combined the forward and reverse predictions for each possible SNP position by averaging the two predictions.

Our algorithm performed very well on this task. Out of the 24,900 sequence positions represented by p-groups on this chip, 442 were non-conformers. Of these 442, our approach identified 36 as candidate SNPs. Subsequent laboratory experimentation confirmed 24 SNPs, all of which were identified by our software. This full result summarized in the for of a Receiver-Operating-Characteristic (ROC) curve in FIG. 4.

Figure 4:
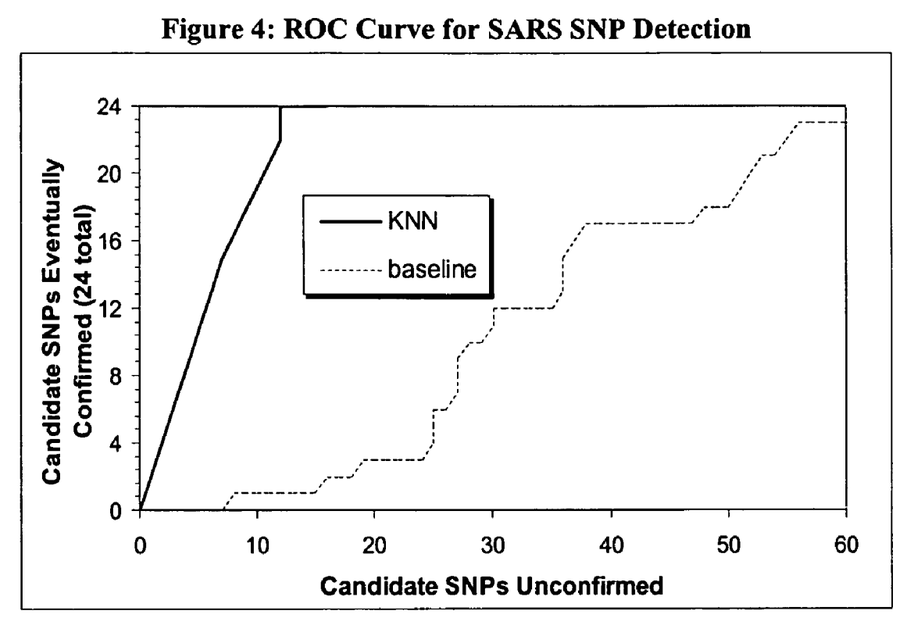
FIG. 4 is a graphical representation of data from the detection of actual SNPs.

A ROC curve is a plot of true positives against false positives. It is obtained by running an algorithm at various thresholds. In the case of the K-nearest-neighbors algorithm, this threshold is the percentage of neighbors that need to be labeled positive examples in order for a non-conforming p-group to be classified a SNP. In this case, false positives are non-SNPs incorrectly classified as SNPS. True positives are SNPs correctly identified by our algorithm. A perfect learner's curve would reach the upper-left corner, since that would mean that the algorithm is capable of identifying all of the true positives without producing any false positives. Though the curve for our algorithm does not quite reach this corner, note that it dominates the baseline algorithm.

Based on the results of this experiment, it seems that the method described here is far superior to the baseline algorithm described above, and is a reliable and efficient method for the identification of SNPs. Remember, however, that this approach classifies some p-groups, namely those whose neighbors are predominantly non-conformers, as non-calls. The percentage of p-groups that are called (either SNP or non-SNP) is also known as the call rate. If this rate is too low, the procedure is useless since the chip cannot be interpreted. So, in order for it to be useful, the software must also result in a good call rate.

Figure 5:
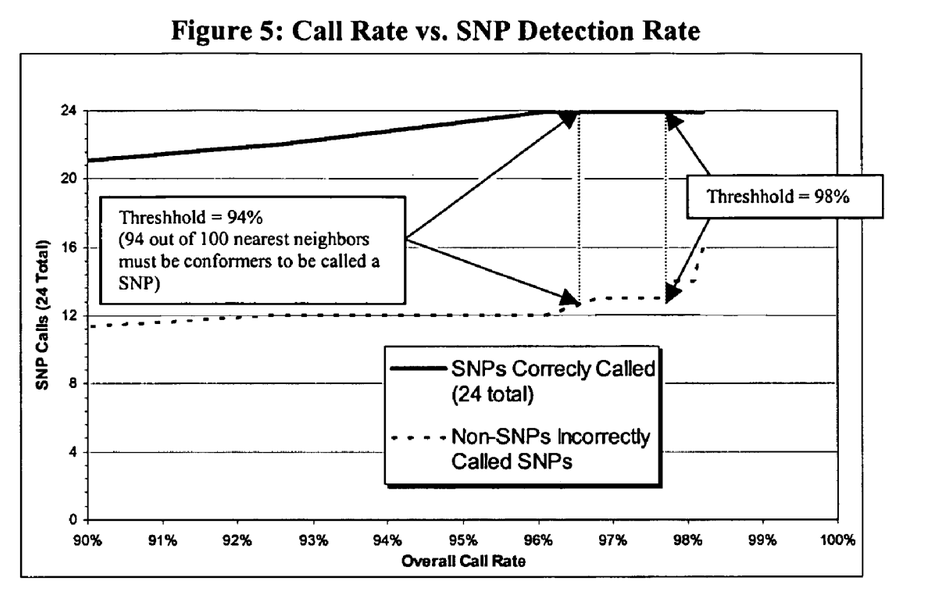
FIG. 5 is a graphical representation of data showing the call rate against the detection rate for SNPs.

In order to adjust the call rate, the threshold value, as described above, can be used. As illustrated in FIG. 5, our approach successfully keeps the call rate over 97% for thresholds between 94% and 98% that easily identify all of the SNPs in the sample and misclassify only a small number of non-SNPs.

TABLE 1

The Features Used to Describe the p-Groups

Reference Sequence: AGCTTTAAGCATATATCGATCGTAGCATACGATCTTTATACTTACATTACCCT...

Resequencing probes (Reference probes in bold)

| | | |
|---|---|---|
| ... | ... | ... |
| P-group 7: | AAGCATATATCAATCCTAGCATAC | ← Probe 7A |
| | AAGCATATATCCATCCTAGCATAC | ← Probe 7C |
| | AAGCATATATCGATCCTAGCATAC | ← Probe 7G |
| | AAGCATATATCTATCCTAGCATAC | ← Probe 7T |
| P-group 8: | AGCATATATCGATCCTAGCATACG | ← Probe 8A |
| | AGCATATATCGCTCCTAGCATACG | ← Probe 8C |
| | AGCATATATCGGTCCTAGCATACG | ← Probe 8G |
| | AGCATATATCGTTCCTAGCATACG | ← Probe 8T |

TABLE 1-continued

The Features Used to Describe the p-Groups

```
P-group 9:      GCATATATCGAACCTAGCATACGA    ← Probe 9A
                GCATATATCGACCCTAGCATACGA    ← Probe 9C
                GCATATATCGAGCCTAGCATACGA    ← Probe 9G
                GCATATATCGATCCTAGCATACGA    ← Probe 9T
      ...                ...                    ...
```

Resulting Intensities (obtained by exposing the chip to the sample)

| Probe | Intensity | |
|---|---|---|
| ... | ... | |
| 7A | 1543 | |
| 7C | 342 | |
| 7G | 3354 | |
| 7T | 737 | |
| 8A | 1456 | ← Note that, though the reference probe from p-group 8 is |
| 8C | 2432 | ← 8A, the highest intensity probe from this |
| | | p-group is 8C. We call such a p-group a nonconformer. |
| 8G | 212 | |
| 8T | 334 | |
| 9A | 332 | |
| 9C | 456 | |
| 9G | 232 | |
| 9T | 2443 | |
| ... | ... | |

The Feature Set:

Each p-group produces one example. The features are the reference base and the four sorted intensities (note that the learner is given no information about which actual probe has the highest intensity). Whether or not this p-group's highest intensity probe is the reference base, that is whether or not this p-group is a conformer, is the category of the example.

| Example | Reference Base | Intensity 1 | Intensity 2 | Intensity 3 | Intensity 4 | conformer? (category) |
|---|---|---|---|---|---|---|
| ... | ... | ... | ... | ... | ... | ... |
| 7 | G | 3354 | 1543 | 737 | 342 | TRUE |
| 8 | A | 2435 | 1456 | 334 | 212 | FALSE |
| 9 | T | 2443 | 456 | 332 | 232 | TRUE |
| ... | ... | ... | ... | ... | ... | ... |

TABLE 2

Our Algorithm

Call each p-group an example
For each example
    Train the classifier on rest of the data
    Predict the category of the example
    If the prediction = non-conformer
        Classify this example as a non-call
    Else
        If the actual category of this example = conformer
            Classify this example as a non-SNP
        Else
            Classify this example as a candidate SNP

TABLE 3

A Baseline Algorithm

Call each p-group an example
For each example
    Let MaxIntensity = intensity of the highest intensity base in this example
    Let SecondIntensity = intensity of the second highest intensity base in this example
    If (MaxIntensity/SecondIntensity) < threshold
        Classify this example as a non-call
    Else
        If the actual category of this example = conformer
            Classify this example as a non-SNP
        Else
            Classify this example as a candidate SNP

We claim:

1. A method for identifying in a sample single nucleotide polymorphisms relative to a reference nucleotide at a position in a reference sequence, the method comprising the steps of:
   hybridizing the sample to a microarray of oligonucleotide probes, the microarray comprising, for each reference nucleotide, a first probe complementary to the reference sequence and second, third and fourth probes complementary to the reference sequence except for a nonmatching nucleotide at the position, the four probes defining a position group at a physical space on the microarray, the nucleotide at the position on each probe in the position group being unique and being selected from the group consisting of A, G, C and T;
   determining the relative hybridization intensity of each probe in each position group;
   classifying each position group as a conformer if the highest intensity probe conforms to the reference sequence at the position, as a nonconformer if the highest intensity probe does not conform to the reference sequence at the position;
   mapping the conformers and nonconformers to their physical space on the microarray;
   identifying as possible SNPs only those nonconformers physically located adjacent on the microarray to conformers; and
   outputting the identification of possible SNPs to a user.

2. A method as claimed in claim 1 wherein said mapping comprises using a machine learning algorithm to map the conformers and nonconformers.

3. A method as claimed in claim 2 wherein the machine learning algorithm is a nearest neighbor algorithm.

4. A method as claimed in claim 1 wherein the position is at a central position of each probe in the position group.

* * * * *